United States Patent [19]
Yamanaka

[11] Patent Number: 5,234,401
[45] Date of Patent: Aug. 10, 1993

[54] PENIS ERECTION ASSISTING DEVICE

[76] Inventor: Hideo Yamanaka, 8-20, Megurohoncho 4-chome, Meguro-ku, Tokyo, Japan

[21] Appl. No.: 17,680

[22] Filed: Feb. 11, 1993

[30] Foreign Application Priority Data

Feb. 13, 1992 [JP] Japan .............................. 4-005586[U]

[51] Int. Cl.⁵ .............................................. A61F 5/41
[52] U.S. Cl. .......................................... 600/38; 600/41
[58] Field of Search .............................. 600/38, 39, 41

[56] References Cited

U.S. PATENT DOCUMENTS

| | | | |
|---|---|---|---|
| 3,495,589 | 2/1970 | Clement | 600/38 |
| 3,744,486 | 7/1973 | Wilson | 600/38 |
| 4,641,638 | 2/1987 | Perry | 128/79 |
| 4,856,498 | 8/1989 | Osbon | 600/38 |
| 4,856,499 | 8/1989 | Kelly | 600/38 |

Primary Examiner—Cary E. O'Connor
Attorney, Agent, or Firm—Malcolm B. Wittenberg

[57] ABSTRACT

A penis erection assisting device contains a sealing member for sealingly accommodating a penis therein, the sealing member having an opening at one end thereof to insert the penis, an extracting hose connected to the sealing member and a pump for extracting air within the sealing member, an expandable circular bag member provided at the opening of the sealing member, and an exhaling hose for supplying air extracted by the pump into the circular bag member to expand the circular bag member.

17 Claims, 2 Drawing Sheets

PENIS ERECTION ASSISTING DEVICE

BACKGROUND OF THE INVENTION

This invention relates to a penis erection assisting device, and more particularly, to a penis erection assisting device which can train the user to make natural erection motion of his penis.

There are many men who become impotent at their young age by various factors, such as stress and so on. Their affliction is very serious, and many devices have been provided and put on the market which prompts erection motion of the penis to cure them of the impotence.

For example, Japanese Laid-open Utility Model Application No. 3-96814 discloses a typical penis erection assist which comprises a cylindrical body made of a transparent plastic material, the front end of which has an opening for insertion of the penis, and the rear end of which is connected to one end of a rubber hose, the other end of which is connected to a vacuum pump with a check valve. The penis erection assist further comprises an elastic member near the opening of the cylindrical body for insertion of the penis to squeeze the proximal portion of the penis after the erection and to keep its erection condition, as well as to connect the circumference of the penis with the opening in a sealed condition. The elastic member has a circular squeezing ring with a larger inner diameter than the outer diameter of the penis in the non-erected state and a cylindrical portion which touches the circumference of the penis tightly.

In case of its use, a penis is inserted in the cylindrical body which has an elastic member near the opening, in such a way that the proximal portion of the penis is positioned at the inner surface of the elastic ring. After the cylindrical portion of the elastic member is touched tightly with the circumference of the penis, the air in the cylindrical body is extracted by the vacuum pump so that the penis is also drawn and thus the sponge body of the penis is actuated to be filled with blood to thereby erect the penis. At this time, the erected penis is squeezed with the ring so that the erected state can be maintained.

However, the above conventional device cannot actuate to erect a penis in case that the patient of impotence is so serious that his penis cannot be erected even if it is drawn, or in case that the diameter of the user's penis is still smaller that the inner diameter of the ring when it is erected, because the penis is squeezed by the elastic ring after the penis has been erected.

Furthermore, the above conventional device cannot afford the user a natural erecting motion in such a way that the sponge body of the penis is filled with blood gradually followed by becoming rigid and swollen, because the elastic member only squeeze the erected penis at a breath with equal strength. It cannot, therefore, be said that the device is enough to make the patient master the natural motion to cure the impotence.

SUMMARY OF THE INVENTION

An object of the invention is to provide a penis erection assisting device which can cure the impotence by providing natural erect motion and making the user master this motion.

The above and other objects of the invention will become apparent from the following description.

According to the invention there is provided a penis erection assisting device comprising sealing means for sealingly accommodating a penis therein, the sealing means having an opening at one end thereof to insert the penis, extracting means connected to the sealing means for extracting air within the sealing means, an expandable circular bag member provided at the opening of said sealing means, and exhaling means for supplying extracted air by the extracting means into the circular bag member to expand the circular bag member.

PREFERRED EMBODIMENT OF THE INVENTION

Figure 1:
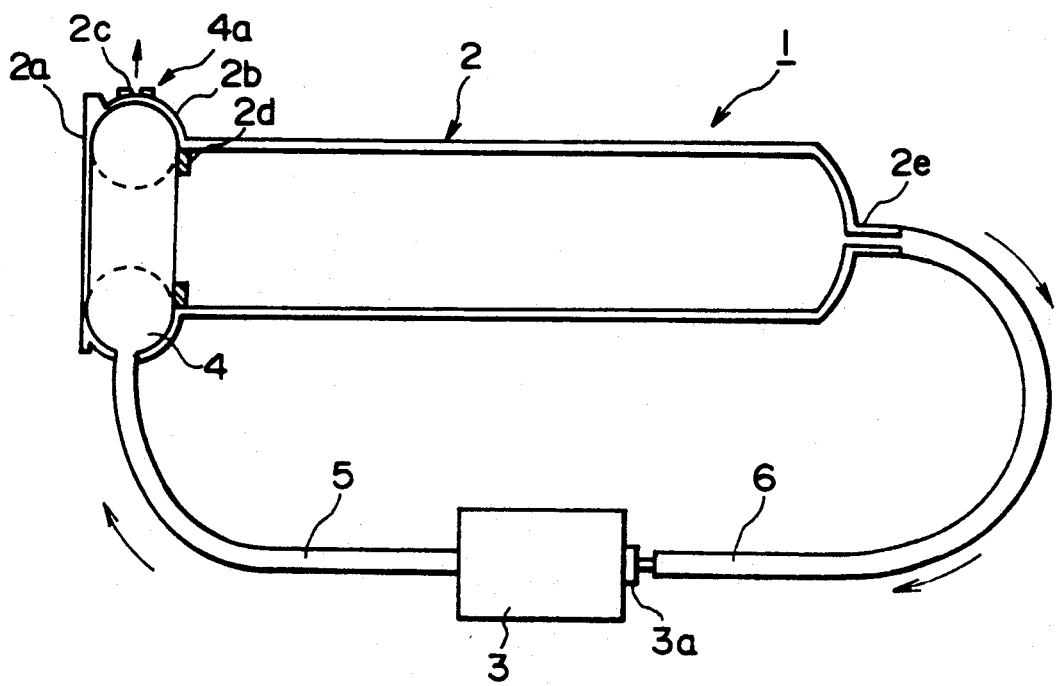
FIG. 1 is a side view schematically showing a penis erection assisting device according to the invention.

Referring to FIG. 1, the penis erection assist 1 comprises a cylinder 2 having an opening 2a for insertion of the penis at one end, an inhaling hose 6 connected to the other end of the cylinder 2, a vacuum pump 3 which draws the inserted penis by extracting the air within the cylinder 2 through the inhaling hose 6 connected to the pump 3, an expandable circular bag 4 provided at the opening 2a, and an exhaling hose 5 connected between the circular bag 4 and the vacuum pump 3 to expand the circular bag 4.

The cylinder 2 made of plastic material has a radially outwardly swollen part 2b for holding the circular bag 4, an opening 2c provided at the swollen part 2b for exposing a vent valve 4a mentioned later, and a circular stopper 2d protruding radially inwardly for preventing the circular bag 4 from riding over the swollen part 2b, and coming into the inside of the cylinder 2, and an inhaling port 2e connected to the inhaling hose 6 at the other end of the cylinder 2.

The vacuum pump 3 is a hollow body made of an elastic material such as rubber, and extracts air within the cylinder 2 through the inhaling hose 6 by repeating squeezing action of the pump 3. A check valve 3a is provided inside the vacuum pump 3 so that the extracted air is prevented from flowing backward again through the inhaling hose 6.

Figure 2:
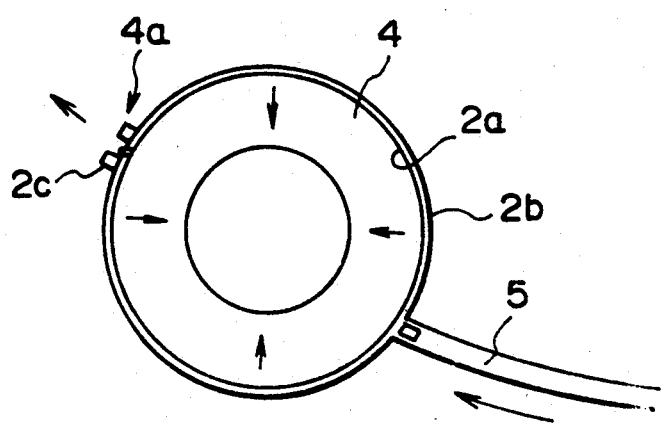
FIG. 2 is a schematic view of the penis erection assisting device of FIG. 1 which is seen from the opening end.

The circular bag 4 is a hollow body made of an expandable elastic material such as rubber. A vent valve 4a (see FIG. 2) protrudes from the circumference of the circular bag 4. The inner air is automatically discharged when the inner air pressure exceeds a predetermined air pressure value. This vent valve 4a may also be opened manually, and it is possible to adjust the inner air pressure to a desired value.

Next, the operation of the penis erection assist 1 is explained. The air within the cylinder 2 is extracted through the inhaling hose 6 by actuating the vacuum pump 3, and then the extracted air flows into the circular bag 4 through the exhaling hose 5 a little later than the time when extracting force grows within the cylinder 2. The cylinder bag 4 is inwardly expanded in the radial direction (see FIG. 2).

Figure 3:
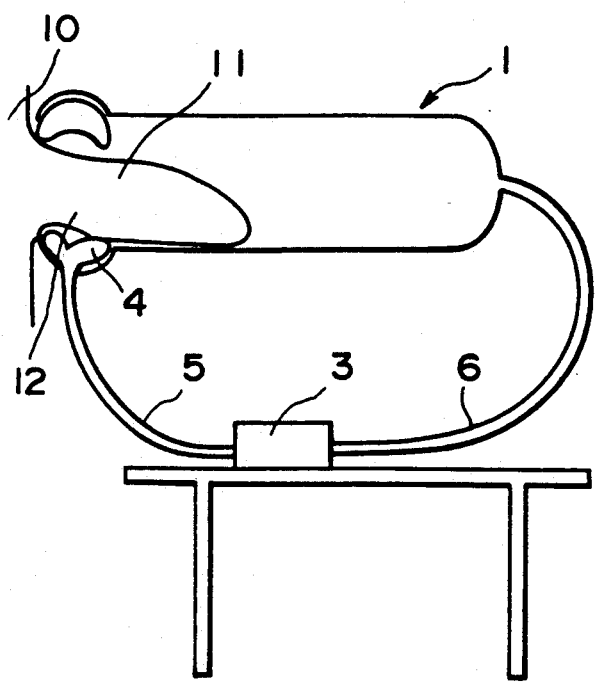
FIG. 3 is a schematic view showing the penis erection assisting device of FIG. 1 into which the user's penis is inserted.
Figure 4:
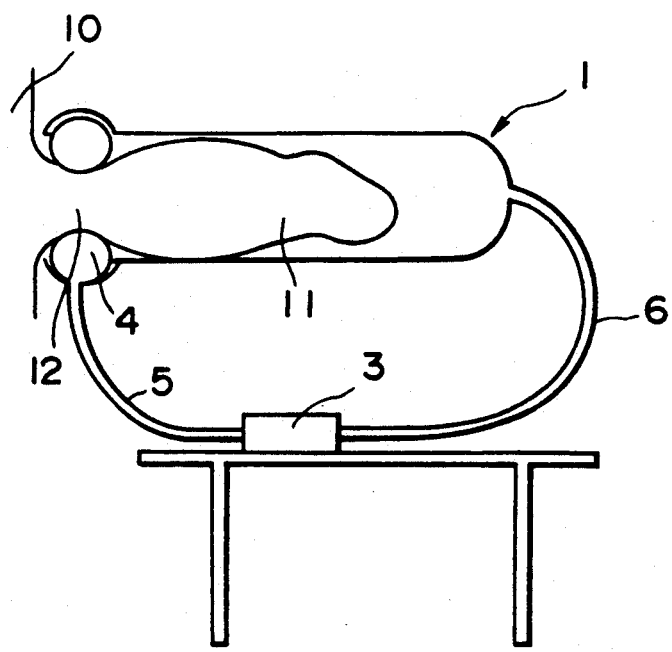
FIG. 4 is a schematic view showing the penis erection assisting device of FIG. 3 with the penis being erected.

Referring to FIGS. 3 and 4, how to use the penis erection assist 1 will be described. First of all, a user 10 inserts his penis 11 into the cylinder 2 through the opening 2a after thoroughly discharging the air within the circular bag 4 through the vent valve 4a to shrink the circular bag 4. He then positions the proximal portion 12 of his penis 11 at the inner circumference of the shrinked circular bag 4 (see FIG. 3). Next, the user 10 actuates the vacuum pump 3 to draw the penis 11, while at the same time to expand the circular bag 4 gradually in such a way as mentioned above, so that the outer surface of the proximal portion 12 is gradually squeezed inwardly in the radial direction (see FIG. 4). In this manner, as blood vessels (vein) under the skin through which the blood is returned from the sponge body of the penis 11 are depressed, the returning blood decreases gradually, and natural erect motion is obtained as the blood is filled in the sponge body to erect the penis 11. At this time, if the outer surface of the proximal portion 12 is squeezed too much by furthermore actuating the vacuum pump 3, it is possible to adjust the strength of squeezing force by extracting the air within the circular bag 4 through the vent valve 4a.

While the vacuum pump 3 which can be operated manually is used as extracting means in this embodiment, an electric motor pump using a chargable type battery or a commercial electric source can also be used. Thus, the extracting means is not limited to any type as far as the air can be extracted. If the electric motor is used, a timer switch may be provided separately to set proper time duration (three to five minutes) to extract the air.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A penis erection assisting device comprising sealing means for sealingly accommodating a penis therein, said sealing means having an opening at one end thereof to insert the penis, extracting means connected to said sealing means for extracting air within said sealing means, an expandable circular bag member provided at the opening of said sealing means, and exhaling means for supplying extracted air by said extracting means into said circular bag member to expand said circular bag member.

2. A penis erection assisting device according to claim 1 further comprising fixing means for fixing said circular bag member at the opening of said sealing means.

3. A penis erection assisting device according to claim 2 in which said fixing means comprises a swollen part bulging outwardly and provided at the opening of said sealing means.

4. A penis erection assisting device according to claim 2 in which said fixing means further comprises a circular stopper provided inside the sealing means.

5. A penis erection assisting device according to claim 1 in which said sealing means comprises a cylinder made of a transparent material.

6. A penis erection assisting device according to claim 1 in which said extracting means comprises an inhaling hose connected to said sealing means and a vacuum pump connected to said inhaling hose.

7. A penis erection assisting device according to claim 6 in which said vacuum pump is made of an elastic material.

8. A penis erection assisting device according to claim 1 in which said extracting means comprises an air back-flow preventing member.

9. A penis erection assisting device according to claim 1 in which said extracting means comprises manually operable extracting means.

10. A penis erection assisting device according to claim 1 in which said extracting means comprises electrically operable extracting means.

11. A penis erection assisting device according to claim 1 in which said circular bag member is made of an elastic material.

12. A penis erection assisting device according to claim 1 in which said circular bag member comprises vent means for discharging air automatically when air pressure within said circular bag member exceeds a predetermined value.

13. A penis erection assisting device according to claim 12 in which said vent means comprises a vent valve.

14. A penis erection assisting device according to claim 1 in which said circular bag member comprises adjusting means for manually regulating air pressure within said circular bag member.

15. A penis erection assisting device according to claim 14 in which said adjusting means comprises a vent valve.

16. A penis erection assisting device according to claim 1 in which said exhaling means comprises an exhaling hose connected between said extracting means and said circular bag member.

17. A penis erection assisting device according to claim 1 in which said extracting means is connected to the other end of said sealing means.

* * * * *